(12) United States Patent  
Gonzales et al.

(10) Patent No.: US 9,078,634 B2
(45) Date of Patent: Jul. 14, 2015

(54) APPARATUS AND METHODS FOR TREATMENT OF OBSTRUCTIVE SLEEP APNEA UTILIZING CRYOLYSIS OF ADIPOSE TISSUES

(75) Inventors: Donald A. Gonzales, San Antonio, TX (US); Anthony Natale, New Preston, CT (US)

(73) Assignee: CRYOSA, LLC, Austin, TX (US)

( * ) Notice: Subject to any disclaimer, the term of this patent is extended or adjusted under 35 U.S.C. 154(b) by 780 days.

(21) Appl. No.: 13/359,000

(22) Filed: Jan. 26, 2012

(65) Prior Publication Data

US 2012/0197361 A1 Aug. 2, 2012

Related U.S. Application Data

(60) Provisional application No. 61/436,712, filed on Jan. 27, 2011, provisional application No. 61/441,207, filed on Feb. 9, 2011.

(51) Int. Cl.
*A61F 7/12* (2006.01)
*A61B 18/02* (2006.01)
*A61B 18/00* (2006.01)

(52) U.S. Cl.
CPC ....... *A61B 18/02* (2013.01); *A61B 2018/00291* (2013.01); *A61B 2018/00464* (2013.01); *A61B 2018/00642* (2013.01); *A61B 2018/00714* (2013.01); *A61B 2018/00791* (2013.01);
(Continued)

(58) Field of Classification Search
CPC .......... A61B 2018/00577; A61B 2018/00791; A61B 2018/00583; A61B 2018/00327; A61B 2017/00084; A61B 18/02; A61B 2018/0212; A61B 19/20; A61B 2018/0262; A61B 18/0218; A61B 5/01; A61B 17/00; A61B 2018/00011; A61B 18/00; A61B 2018/00005; A61B 2018/00053; A61B 2018/0063; A61B 2018/00744; A61B 2018/00863; A61B 5/145; A61B 5/14503; A61F 2007/0063; A61F 5/08; A61N 2005/007; A61N 1/00
USPC ......................................... 606/20–23, 25–26
See application file for complete search history.

(56) References Cited

U.S. PATENT DOCUMENTS 5,245,023 A  9/1993 Peoples et al.
5,250,430 A  10/1993 Peoples et al.
(Continued)

FOREIGN PATENT DOCUMENTS

JP  1223961  9/1989
WO  9903411 A1  1/1999
(Continued)

OTHER PUBLICATIONS

International Search Report for International Application No. PCT/US2012/022697, issued on May 16, 2012 and mailed Aug. 20, 2012.
(Continued)

*Primary Examiner* — Deborah Malamud
(74) *Attorney, Agent, or Firm* — Choate, Hall & Stewart LLP

(57) ABSTRACT

Methods, devices, and systems employ cryolysis of oropharyngeal adipose tissues to selectively remove fat cells from the tissues causing obstructive sleep apnea. In various embodiments, a chilled liquid—e.g., a liquid or air—is applied to the target tissue at a temperature and for a duration sufficient to cause cryolysis.

18 Claims, 10 Drawing Sheets

(52) U.S. Cl.
CPC . *A61B2018/0212* (2013.01); *A61B 2018/0262* (2013.01); *A61B 2018/0293* (2013.01)

(56) References Cited

U.S. PATENT DOCUMENTS

| | | | |
|---|---|---|---|
| 5,534,432 | A | 7/1996 | Peoples et al. |
| 5,663,063 | A | 9/1997 | Peoples et al. |
| 6,032,675 | A | 3/2000 | Rubinsky |
| 6,041,787 | A | 3/2000 | Rubinsky |
| 6,126,657 | A | 10/2000 | Edwards et al. |
| 6,245,537 | B1 | 6/2001 | Williams et al. |
| 6,316,262 | B1 | 11/2001 | Huisman et al. |
| 6,378,525 | B1 | 4/2002 | Beyar et al. |
| 6,514,515 | B1 | 2/2003 | Williams |
| 6,548,569 | B1 | 4/2003 | Williams et al. |
| 6,555,123 | B2 | 4/2003 | Williams et al. |
| 6,585,994 | B2 | 7/2003 | Williams et al. |
| 6,592,892 | B1 | 7/2003 | Williams |
| 6,593,116 | B1 | 7/2003 | Huisman et al. |
| 6,610,764 | B1 | 8/2003 | Martin et al. |
| 6,623,749 | B2 | 9/2003 | Williams et al. |
| 6,689,589 | B2 | 2/2004 | Huisman et al. |
| 6,746,447 | B2 | 6/2004 | Davison et al. |
| 6,746,685 | B2 | 6/2004 | Williams |
| 6,828,357 | B1 | 12/2004 | Martin et al. |
| 6,838,493 | B2 | 1/2005 | Williams et al. |
| 6,867,247 | B2 | 3/2005 | Williams et al. |
| 6,867,248 | B1 | 3/2005 | Martin et al. |
| 6,878,758 | B2 | 4/2005 | Martin et al. |
| D568,258 | S | 5/2008 | Adam |
| 7,367,341 | B2 | 5/2008 | Anderson et al. |
| 7,842,029 | B2 | 11/2010 | Anderson et al. |
| 7,850,683 | B2 | 12/2010 | Elkins et al. |
| 7,854,754 | B2 | 12/2010 | Ting et al. |
| 8,192,474 | B2 | 6/2012 | Levinson |
| 8,275,442 | B2 | 9/2012 | Allison |
| 8,285,390 | B2 | 10/2012 | Levinson et al. |
| 8,337,539 | B2 | 12/2012 | Ting et al. |
| 8,523,927 | B2 | 9/2013 | Levinson et al. |
| 8,603,073 | B2 | 12/2013 | Allison |
| 8,676,338 | B2 | 3/2014 | Levinson |
| 8,702,774 | B2 | 4/2014 | Baker et al. |
| 8,834,547 | B2 | 9/2014 | Anderson et al. |
| 8,840,608 | B2 | 9/2014 | Anderson et al. |
| 2002/0164729 | A1 | 11/2002 | Skraly et al. |
| 2004/0234576 | A1 | 11/2004 | Martin et al. |
| 2007/0010861 | A1 | 1/2007 | Anderson et al. |
| 2007/0198071 | A1 | 8/2007 | Ting et al. |
| 2007/0255362 | A1 | 11/2007 | Levinson et al. |
| 2007/0270925 | A1 | 11/2007 | Levinson |
| 2008/0077201 | A1 | 3/2008 | Levinson et al. |
| 2008/0077202 | A1 | 3/2008 | Levinson |
| 2008/0077211 | A1 | 3/2008 | Levinson et al. |
| 2008/0200910 | A1 | 8/2008 | Burger et al. |
| 2008/0287839 | A1 | 11/2008 | Rosen et al. |
| 2009/0018623 | A1 | 1/2009 | Levinson et al. |
| 2009/0018624 | A1 | 1/2009 | Levinson et al. |
| 2009/0018625 | A1 | 1/2009 | Levinson et al. |
| 2009/0018626 | A1 | 1/2009 | Levinson et al. |
| 2009/0018627 | A1 | 1/2009 | Levinson et al. |
| 2009/0118722 | A1 | 5/2009 | Ebbers et al. |
| 2009/0149929 | A1 | 6/2009 | Levinson et al. |
| 2009/0192504 | A1 | 7/2009 | Askew |
| 2010/0057065 | A1 | 3/2010 | Krimsky |
| 2010/0081971 | A1 | 4/2010 | Allison |
| 2010/0152824 | A1 | 6/2010 | Allison |
| 2010/0280582 | A1 | 11/2010 | Baker et al. |
| 2011/0066216 | A1 | 3/2011 | Ting et al. |
| 2011/0238050 | A1 | 9/2011 | Allison et al. |
| 2011/0238051 | A1 | 9/2011 | Levinson et al. |
| 2011/0300079 | A1 | 12/2011 | Martens et al. |
| 2012/0022518 | A1 | 1/2012 | Levinson |
| 2012/0239123 | A1 | 9/2012 | Weber et al. |
| 2013/0066309 | A1 | 3/2013 | Levinson |
| 2013/0079684 | A1 | 3/2013 | Rosen et al. |
| 2013/0116758 | A1 | 5/2013 | Levinson et al. |
| 2013/0116759 | A1 | 5/2013 | Levinson et al. |
| 2013/0158440 | A1 | 6/2013 | Allison |
| 2013/0158636 | A1 | 6/2013 | Ting et al. |
| 2013/0245731 | A1 | 9/2013 | Allison |
| 2013/0253384 | A1 | 9/2013 | Anderson et al. |
| 2013/0253494 | A1 | 9/2013 | Anderson et al. |
| 2013/0253495 | A1 | 9/2013 | Anderson et al. |
| 2013/0253496 | A1 | 9/2013 | Anderson et al. |
| 2014/0005760 | A1 | 1/2014 | Levinson et al. |
| 2014/0067025 | A1 | 3/2014 | Levinson et al. |
| 2014/0257443 | A1 | 9/2014 | Baker et al. |
| 2014/0277219 | A1 | 9/2014 | Nanda |
| 2014/0277302 | A1 | 9/2014 | Weber et al. |
| 2014/0316393 | A1 | 10/2014 | Levinson |

FOREIGN PATENT DOCUMENTS

| | | |
|---|---|---|
| WO | WO-03/078596 | 9/2003 |
| WO | WO-2007/101039 A1 | 9/2007 |
| WO | WO-2007/133839 A1 | 11/2007 |
| WO | WO-2007127924 A2 | 11/2007 |
| WO | WO-2008/039556 A1 | 4/2008 |
| WO | WO-2008/039557 A1 | 4/2008 |
| WO | WO-2008/055243 A2 | 5/2008 |
| WO | WO-2008/060423 A2 | 5/2008 |
| WO | WO-2008/143678 A1 | 11/2008 |
| WO | WO-2009/011708 A1 | 1/2009 |
| WO | WO-2009/026471 A1 | 2/2009 |
| WO | WO-2010/036732 A1 | 4/2010 |
| WO | WO-2010/127315 A2 | 11/2010 |
| WO | WO-2011/091293 A1 | 7/2011 |
| WO | WO-2011/091431 A1 | 7/2011 |
| WO | WO-2012/012296 A1 | 1/2012 |
| WO | WO-2012/103242 A1 | 8/2012 |
| WO | WO-2014/151850 A2 | 9/2014 |
| WO | WO-2014/151872 A2 | 9/2014 |

OTHER PUBLICATIONS

Avram, M.M. And Harry, R.S., Cryolipolysis for Subcutaneous Fat Layer Reduction, Lasers in Surgery and Medicine, 41: 703-708 (2009).

Coleman, S.R. et al., Clinical Efficacy of Noninvasive Cryolipolysis and Its Effects on Peripheral Nerves, Aesth. Plast. Surg., 33: 482-488 (2009).

Nelson, A.A. et al., Cryolipolysis for Reduction of Excess Adipose Tissue, Semin. Cutan. Med. Surg., 28: 244-249 (2009).

Zelickson, B. et al., Cryolipolysis for Noninvasive Fat Cell Destruction: Initial Results from a Pig Model, Dermatol. Surg., 35: 1462-1470 (2009).

APPARATUS AND METHODS FOR TREATMENT OF OBSTRUCTIVE SLEEP APNEA UTILIZING CRYOLYSIS OF ADIPOSE TISSUES

CROSS-REFERENCE TO RELATED APPLICATIONS

This application claims priority to and the benefits of, and incorporates by reference herein, U.S. Ser. Nos. 61/436,712 (filed Jan. 27, 2011) and 61/441,207 (filed Feb. 9, 2011).

BACKGROUND

1. Field of the Invention

The present invention relates generally to cryolytic treatment of obstructive sleep apnea.

2. Description of Related Art

Obstructive sleep apnea (OSA) is disease that affects up to 20% of the adult population. OSA generally occurs during sleep when soft tissue obstructs the airway and creates cessation of, or impedes, breathing. Obstruction can occur at one or more levels including the retropalatal and retrolingual areas. Surgical correction of such obstructions remains a challenge, specifically for the retrolingual area. Removal or ablation of tongue tissue has been utilized with poor results due to complications, such as severe bleeding, abscess formation, and/or the inability to move the tongue anterior enough to relieve the obstruction.

It is known that patients with OSA have a higher percentage of adipose deposits in the areas of obstruction, specifically, the soft palate and uvula, base of tongue and lateral pharyngeal walls. The adipose tissue may be up to or greater than 40% of the total volume of tissues in these areas. Removal of the fat deposits in these areas would permit relief from OSA symptoms while preserving surrounding tissue. To date, however, cryolytic treatment of OSA has involved procedures analogous to ablation, merely substituting cryolytic cold for electrolytic heat and nonselectively destroying tissue in a similar manner—and with the same complications.

SUMMARY

The present invention employs cryolysis in a tissue-selective manner, selectively removing fat cells from the tissues causing OSA (e.g., oropharyngeal tissues), and exploits the fact that fat cells are more easily damaged by cooling than skin cells.

Lipolysis is presently used to "dissolve" fat cells by nonsurgical means. A number of methods have been attempted for lipolysis including the application of laser radiation, ultrasound, and radiofrequency electric current. Because fat cells are more easily damaged by cooling than the tough outer skin surface, cryolysis of adipose tissues (sometimes referred to as "cryolipolysis") has been employed by cooling tissue via thermal conduction in a controlled fashion—i.e., selecting the temperature level and exposure to avoid skin damage or frostbite and selectively damaging only the underlying fat cells. While the process is not fully understood, it appears that fatty or adipose tissue that is cooled below body temperature but above freezing undergoes localized cell death followed by a local inflammatory response (a local panniculitis) that gradually, over the course of several months, reduces the volume of the fatty tissue layer.

In various embodiments, the present invention exploits the particular cryolytic vulnerability of adipose tissue to treat OSA without damaging and/or reducing the function of oropharyngeal tissue. Certain embodiments may comprise engagement members that are formed in the shape of each specific area to be cooled. Some embodiments may utilize graspers capable of grasping or pinching anatomical structures (soft palate, base of tongue, soft tissue of the pharynx) associated with OSA, thereby cooling the tissue between the gripping portions and ensuring good mechanical contact during cooling. In some embodiments, the cooling device may pierce the mucosa to cool the underlying tissues. The cooling device may also inject a cooling agent into the underlying tissue.

Accordingly, in a first aspect, the invention pertains to a device for treatment of obstructive sleep apnea. In various embodiments, the device comprises a cooling unit for chilling a cooling fluid and an applicator for receiving the cooling fluid; the applicator is configured for contact with oropharyngeal tissue, and the applicator and cooling unit cooperatively cause cooling of the oropharyngeal tissue to a temperature between approximately 5° C. and approximately −25° C. for approximately one to approximately thirty minutes, whereby a volume of adipose tissue in the contacted oropharyngeal tissue is subsequently reduced. In various embodiments, the applicator comprises an engagement member complementary to a target portion of the oropharyngeal tissue, and the applicator further includes a recirculation conduit for facilitating heat transfer between the engagement member and the cooling fluid. In some implementations the engagement member is flexible and conformal, while in other implementations is rigid—e.g., a substantially flat plate; "C"-shaped and complementary to a base of a tongue; or "V"-shaped and configured to engage a soft palate or a uvula. A rigid engagement member may be hinged, and the applicator may further include a control member (such as a wire) facilitating closure of the engagement member to grasp tissue. If desired, the cooling unit may be configured to provide suction to the engagement member to enhance mechanical contact thereof with the oropharyngeal tissue. In other embodiments, the applicator comprises a needle configured for injection of the cooling fluid into the target portion of the oropharyngeal tissue.

In various embodiments, the cooling fluid is a liquid, e.g., a refrigerant or a water and glycerine solution. The cooling unit may be configured for feedback operation to maintain a substantially constant temperature at the target portion of the oropharyngeal tissue. To facilitate this, the applicator may be associated with a temperature sensor to which the cooling unit is responsive.

In other embodiments, the cooling fluid is chilled air. For example, the applicator may comprise a tube for introducing the chilled air into the oropharynx and an inflatable member for sealing the esophagus and preventing the chilled air from entering the lower respiratory tract. In various implementations, the tube comprises inner and outer coaxial lumens, where the inner lumen has a portion extending past an end of the outer lumen and an inflatable member thereon; the cooling unit sends chilled air through the outer lumen and breathable air through the inner lumen. In other embodiments the cooling fluid is a chilled biocompatible liquid, and the applicator comprises a tube for introducing the liquid into the oropharynx and an inflatable member for sealing the esophagus and preventing aspiration.

In the ensuing discussion, any embodiment of any of the present devices methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. The term "consists essentially of" means excluding other materials that contribute to function, unless otherwise defined herein. Nonetheless, such other materials may be present, collectively or individually, in trace amounts.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art. In various embodiments, these terms connote ±10% and in some embodiments ±5%.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps. For example, in a method that comprises providing a tongue-stabilization device, the method includes the specified steps but is not limited to having only those steps. For example, such a method could also include inserting the device through an incision into the tongue of a patient.

Further, a device or structure that is configured in a certain way is configured in at least that way, but it can also be configured in other ways than those specifically described.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

Figure 1:
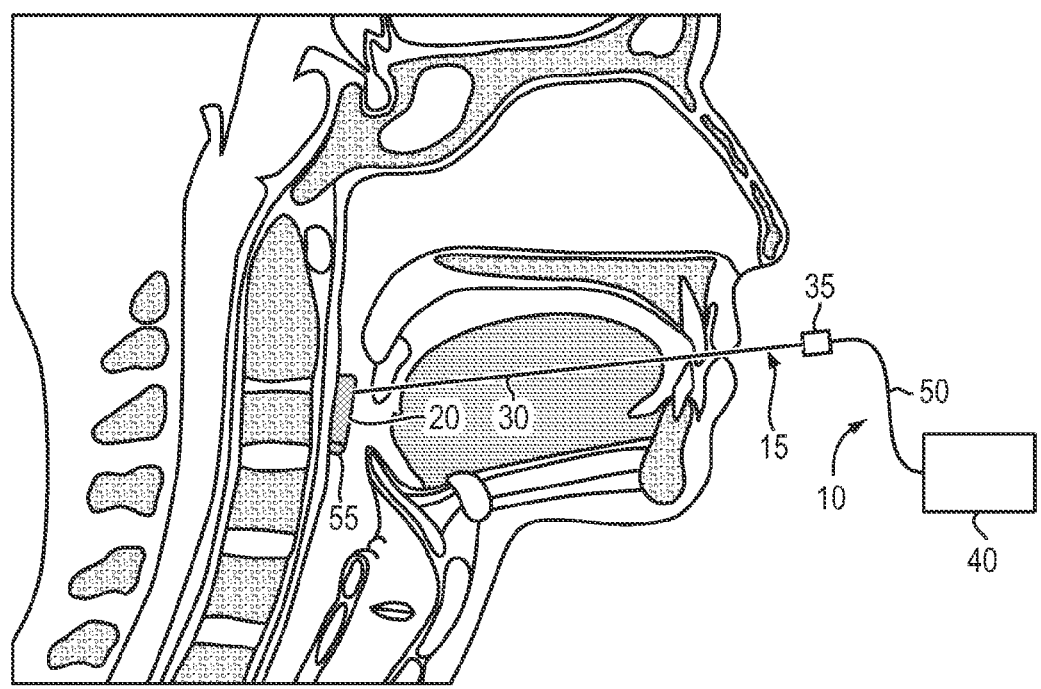
FIG. 1 depicts a side cross-sectional view of a human patient and a first exemplary embodiment of a cooling system.

Referring now to the drawings, and more particularly to FIG. 1, a cooling system 10 comprises a cooling device 15 including an engagement member 20 configured with a substantially flat plate to engage (i.e., rest against) the smooth surface of a patient's pharyngeal wall. In this embodiment cooling device 15 further comprises a shaft portion 30 and a coupling member 35 distal from engagement member 20. The shaft portion 30 is shown, for illustrative convenience, as extending directly from coupling member 35 to engagement member 20. If a straight, rigid shaft portion 30 is in fact employed, in use it would depress the tongue in order to allow engagement member 20 to access the oropharyngeal tissue target. Alternatively, shaft member 35 may be curved to extend over and around the tongue without depression thereof.

Coupling member 35 can be coupled to a cooling unit 40 via a conduit 50. It is understood that in certain exemplary embodiments, cooling device 15 may be used without cooling unit 40 as explained below. In this embodiment, cooling unit 40 can circulate a cooling agent (not visible in the pictures) through conduit 50 and cooling device 15 to maintain a desired temperature at the target tissue. In certain embodiments, cooling device 15 can be cooled to a temperature between approximately 0° C. and −20° C.

More particularly, in one embodiment, shaft portion 30 is a rigid structure having adjacent lumens through which a chilled cooling fluid is continually circulated past engagement member 20, thereby cooling the tissue with which engagement member 20 is in contact (or more accurately, withdrawing heat from the tissue). The lumens terminate in a pair of releasably engageable ports at the proximal end of shaft portion 30. Conduit 50, in this embodiment, comprises a pair of flexible fluid lines each having a separate coupling structure for engaging one of the ports, although the coupling structures are desirably integrated into a single engagement member 35. For example, the coupling structures may be snap-on sockets that receive and releasably engage flanged ends of the shaft ports in a fluid-tight manner; release of conduit 50 from shaft portion 30 may be effected, for example, using a thumb-operated tab on the coupling member 35. Alternatively, each conduit may have its own coupling member (e.g., a threaded cap or other conventional fluid-tight coupling) that individually and releasably engages one of the ports of shaft portion 20. The releasable coupling allows shaft portion 30 and engagement member 20 to be disposable or sterilizable, while conduits 50 are permanent.

Cooling unit 40 continually removes heat from the circulating coolant fluid to a heat sink and continuously provides the chilled coolant to shaft portion 30 and engagement member 20 via one fluid line while withdrawing coolant through the other fluid line. Examples of suitable circulating coolants include water, glycol, synthetic heat transfer fluid, oil, or a refrigerant. In specific embodiments, the coolant comprises or consists essentially of a water and solute solution. In one implementation, the coolant comprises or consists essentially of a water and glycerine solution comprising less than 45% glycerine by weight. The fluid lines of conduit 50 can be hoses made of polyethylene, polyvinyl chloride, polyurethane, or other flexible or rigid material that can accommodate the particular circulating coolant. Cooling unit 40 can be a refrigeration unit, a cooling tower, a thermoelectric chiller, or any other device capable of removing heat from a coolant. For example, cooling unit 40 can include one or more thermoelectric cooling elements, such as Peltier-type thermoelectric elements.

Cooling unit 40 may also include a processor for monitoring process parameters via one or more sensors. For example, a sensor 55 disposed within or against engagement member 20 can report the temperature of the engagement member 20, and the processor of cooling unit 20 may responsively adjust the degree of cooling of the circulating coolant; in this way, a desired temperature (or temperature range) is achieved and maintained in a closed-loop fashion via continuous feedback. The temperature sensor 55 may be connected to cooling unit via a wire along shaft portion 30; the wire terminates in an electrical coupling at the proximal end of shaft portion 30, and this coupling engages a complementary electrical coupling within coupling member 35 (and which is in electrical communication with cooling unit 40). Alternatively, the sensor may be wireless, and the processor of cooling unit 40 equipped to receive wireless signals from the sensor.

Alternatively or in addition, a temperature sensor may be located within cooling unit 40 to monitor the temperature of incoming fluid through one of the fluid lines 50. The relationship between fluid temperature at the sensor and the temperature of engagement member 20 may be determined by calibration, and the output of the sensor once again used in a closed-loop configuration to achieve and maintain a desired estimated temperature at engagement member 20.

The processor may be provided as either software, hardware, or some combination thereof. For example, the processor and control circuitry may be based on a server-class computer, such as a PC having a CPU board containing one or more processors such as the Core Pentium or Celeron family of processors manufactured by Intel Corporation of Santa Clara, Calif. The processor may also include a main memory unit for storing programs and/or data relating to the feedback control described above and more generally to operation of the cooling unit 40 during a procedure. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), or programmable logic devices (PLD). In some embodiments, the programs may be provided using external RAM and/or ROM such as optical disks, magnetic disks, as well as other commonly used storage devices. For embodiments in which the control functions are implemented by a software program, the program may be written in any one of a number of high level languages such as FORTRAN, PASCAL, JAVA, C, C++, C#, LISP, PERL, BASIC, PYTHON or any suitable programming language. Additionally, the software can be implemented in an assembly language and/or machine language directed to a microprocessor.

During use, the engagement member 20 of cooling device 15 makes contact with the surface tissue overlying the adipose tissue of the pharyngeal wall. In exemplary embodiments, engagement member 20 may be placed in contact with the surface tissue for approximately one to thirty minutes. In particular embodiments, engagement member 20 may placed in contact with the surface tissue for approximately 15 minutes. As noted above, cooling device 15 can be cooled to and maintained at a temperature between approximately 0° C. and −20° C. (or, more generally, between approximately −25° C. and 5° C., typically at a selected temperature that is kept within a clinical tolerance range, e.g., ±10% or ±5%) during this contact time. The temperature and time should be sufficient to cause cryolysis of adipose tissues and selectively remove or reduce fat cells from the tissues in the pharyngeal wall; as mentioned earlier, this effect need not be immediate. Reducing the volume of adipose tissue in the pharyngeal wall eliminates or reduces OSA symptoms for the patient.

In certain embodiments, cooling device 15 may include a vacuum unit that provides suction at the engagement member 20 to enhance and maintain mechanical contact with the tissue of the pharyngeal wall. This may also provide a greater effective surface area of contact. For example, suction may be provided by a third lumen running along shaft member 30 but fluidly separate from the lumens through which cooling fluid circulates. The contact surface of engagement member 20 may be perforated to permit the suction to exert its effect across substantially the entire area of the contact surface, with the perforations being small enough to avoid actually drawing the tissue therein and risking damage. The feedback circuitry discussed above can monitor the applied suction both to prevent excessive force from being applied as well as to indicate to the clinician the adequacy of contact between the engagement member 20 and the pharyngeal tissue. This suction capability may be employed in any of the embodiments shown in FIGS. 1-3.

Figure 2:
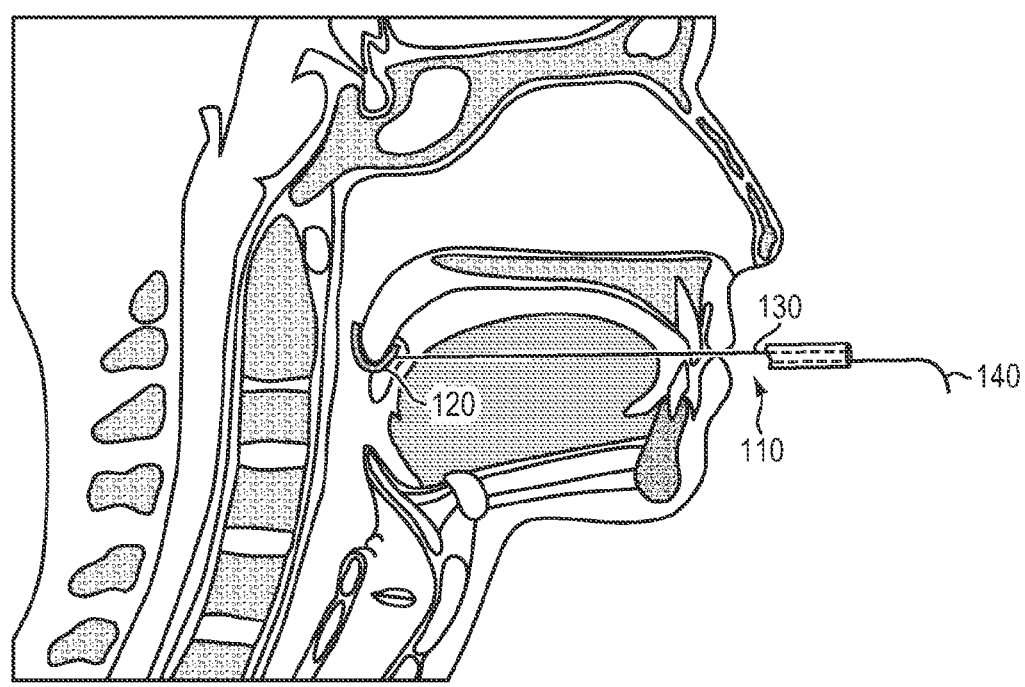
FIG. 2 depicts a side cross-sectional view of a human patient and a second exemplary embodiment of a cooling device.

Refer now to FIG. 2, which illustrates a cooling device 115 that is similar to cooling device 15 described above. In this embodiment cooling device 115 comprises a shaft portion 130 and an engagement member 120. Engagement member 120 has a "V" shape or "U" shape configured to engage the soft palate or uvula. During use, cooling device 115 operates similar to cooling device 15, with the exception that the area treated is in the soft palate and/or uvula, rather than the pharyngeal wall. The engagement member 120, in other words, is uvula-shaped or configured so as to be able to receive and retain the uvula or portion thereof. In one embodiment, the engagement member 120 is configured to be manipulable from an open configuration, which allows the clinician to conveniently cup the uvula within the engagement member 120, to a closed position the surrounds the uvula more snugly. This can be achieved, for example, using a hinged engagement member and a stiff wire 140 that the clinician may extend and retract through a third lumen running along the shaft member 130. The wire operates the engagement member so as, for example, to facilitate its hinged closure via retraction of the wire. Shape-memory alloys such as NITINOL are biocompatible and may be used to form the wire 140.

Figure 3:
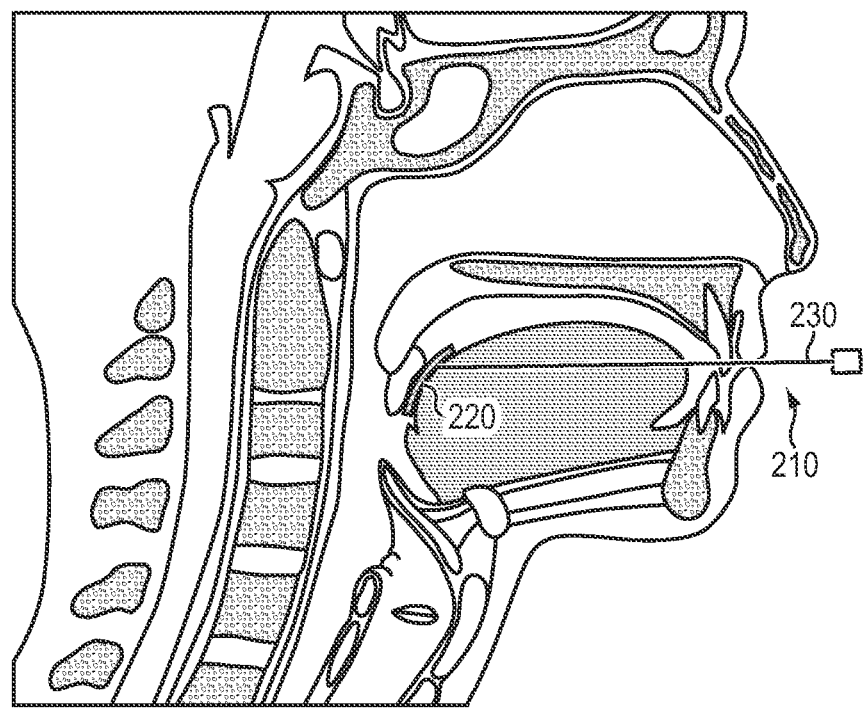
FIG. 3 depicts a side cross-sectional view of a human patient and a third exemplary embodiment of a cooling device.

With reference now to FIG. 3, a cooling device 215 is shown that is similar to cooling device 15 described above. In this embodiment cooling device 215 comprises a shaft portion 130 and an engagement member 220. Engagement member 220 has a "C" shape configured to engage the base of the patient's tongue—e.g., shaped to be complementary to the rear surface of the tongue opposite the uvula. During use, cooling device 215 operates in the manner described above regarding cooling device 15, with the exception that the area treated is in the base of the tongue, rather than the pharyngeal wall. It is understood that the embodiments shown in FIGS. 3 and 4 can be used with or without cooling unit shown in FIG.

1. For example, the cooling device 15 may be stored in a freezer and, following its removal just prior to use, maintain its cold temperature for a sufficient period of time to facilitate treatment as described herein—e.g., by incorporating an "ice pack" gel in or against the engagement member 20. Furthermore, any of the devices shown in FIGS. 1-3 may hinged and operable via a wire to grasp the tissue after contact is established therewith.

In still other embodiments, the engagement member 20 is not rigid but is instead flexible and conformal. For example, engagement member 20 may take the form of a cushion, e.g., a bladder partially filled with air or other fluid so that it is soft and conforms when pressed up against oropharyngeal structures. For example, the fluid filling the bladder may be the same as that circulating through the shaft portion.

Figure 4:
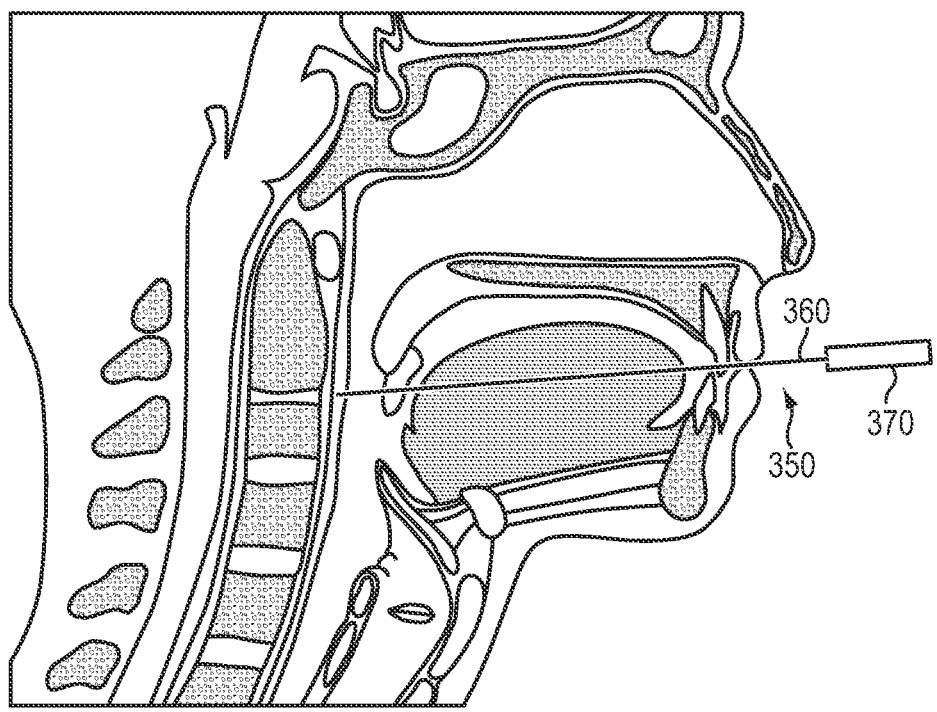
FIG. 4 depicts a side cross-sectional view of a human patient and a fourth exemplary embodiment of a cooling device.

With reference to FIG. 4, a cooling device 350 is configured to inject a cooling agent into the pharyngeal wall. In this embodiment, cooling device 350 comprises a shaft or needle 360 configured to pierce the oropharyngeal tissue and allow the clinican to inject therethrough a cooling agent, which is held at a chilled temperature in a reservoir 370 (e.g., a syringe). In other embodiments, cooling device 350 is coupled to a cooling unit similar to cooling unit 40 (shown in FIG. 1) in order to chill the liquid to the proper temperature, and to alert the clinician when this temperature has been achieved. Injection of the cooling agent causes cryolysis of adipose tissues and selectively removes or reduces fat cells from the tissues in the pharyngeal wall. In this embodiment, the cooling agent may be a water and glycerol mixture or any other physiologically harmless liquid capable of being chilled to the necessary temperature without freezing.

Figure 5:
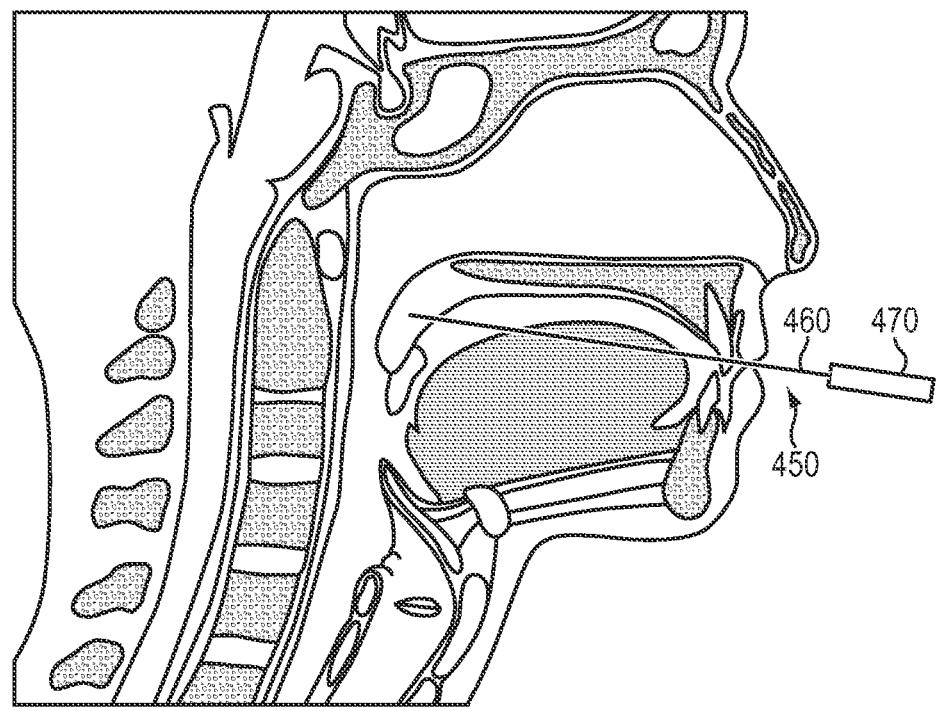
FIG. 5 depicts a side cross-sectional view of a human patient and a fifth exemplary embodiment of a cooling device.

As shown in FIG. 5, the cooling agent may be injected into the soft palate and/or uvula rather than the pharyngeal wall. In particular, a cooling device 450 comprises a shaft or needle 460 configured to inject a cooling agent stored in a reservoir 470 (e.g., a syringe). The operation is as described above in connection with FIG. 4.

Figure 6:
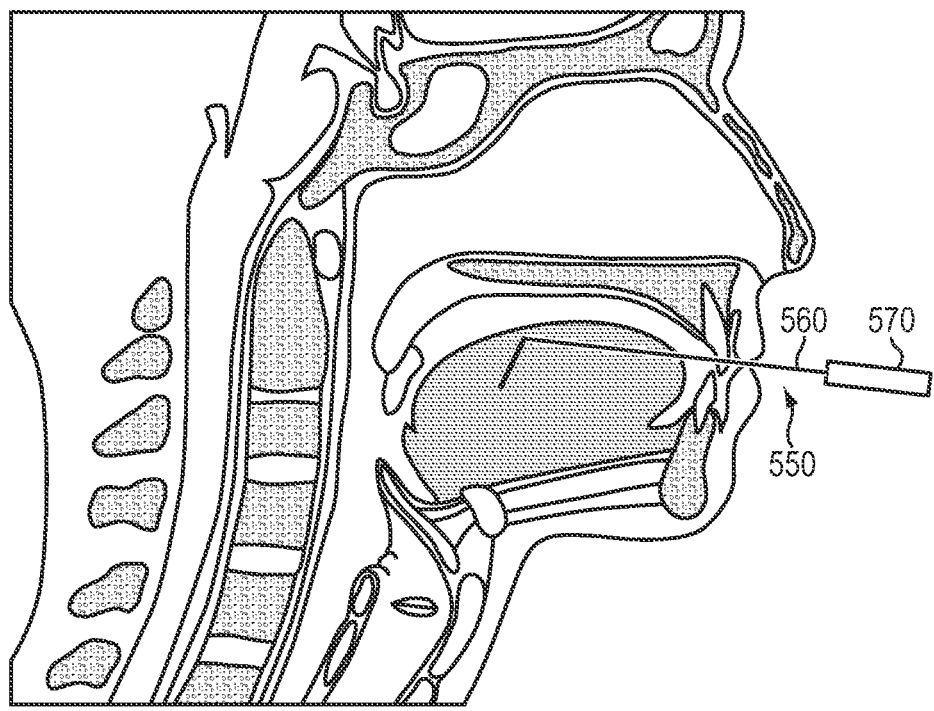
FIG. 6 depicts a side cross-sectional view of a human patient and a sixth exemplary embodiment of a cooling device.

Similarly, with reference to FIG. 6, the cooling agent may be injected into the base of the tongue. In particular, a cooling device 550 has an angled needle 560 shaped for convenient access to the area to be treated; once again the cooling agent is stored in a reservoir 470 (e.g., a syringe), and the operation is as described above in connection with FIG. 4.

Figure 7:
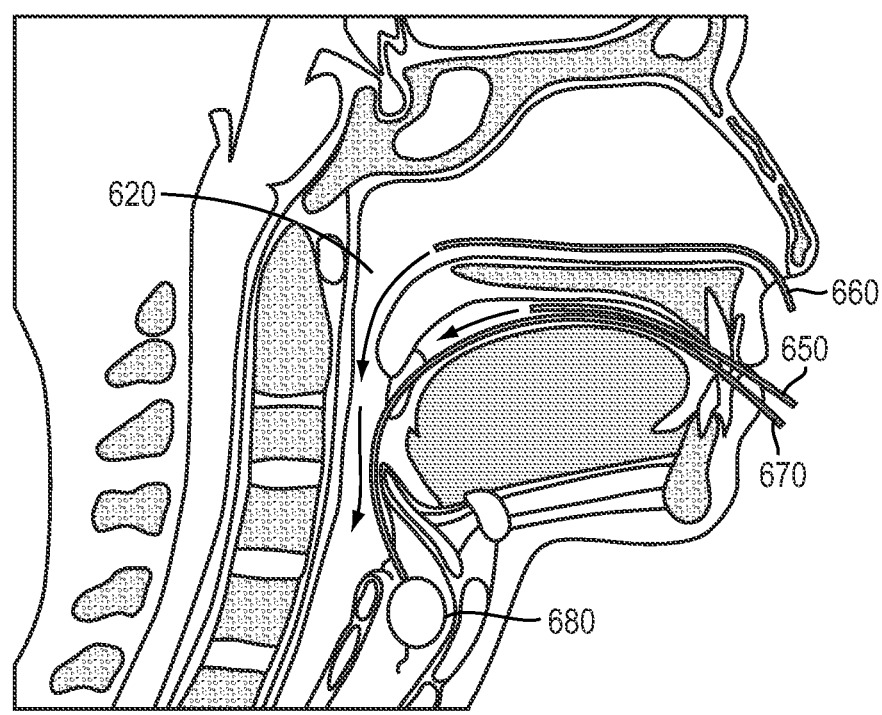
FIG. 7 depicts a side cross-sectional view of a human patient and a seventh exemplary embodiment of a cooling device.

In other embodiments, the tissue to be treated is cooled by means of exposure to chilled air rather than by mechanical contact or injection of a liquid. With reference to FIG. 7, cold air 620 be delivered to the oropharynx via an intraoral tube 650 and/or an intranasal tube 660 (e.g., a nasal cannula). It is understood that certain embodiments may use only an intraoral tube 650, while others may use an intranasal tube 660, while still other embodiments may use both. If cold air 620 is administered through the nasal cavity, the mouth will be closed to maintain the cool temperature. If the cold air is delivered intraorally, the nose will be occluded.

This can be accomplished with the patient awake or under general anesthesia. In certain embodiments, an intubation cuff 670 with an inflatable member 680 can be used to seal the esophagus and prevent cold air from entering the lower respiratory tract. Breathing air can be supplied to the lungs through the intubation cuff 670. The progress of the cooling procedure may be monitored by means of a temperature sensor within the oropharynx, in contact with the tissue to be treated, or introduced via a needle into the interior of that tissue.

In certain embodiments, the cold air is continuously delivered through one conduit and withdrawn via a proximally located conduit to maintain a temperature of approximately −20 to approximately 0° C. in the oropharynx. More generally the temperature in the oropharynx may be maintained between approximately −25° C. and 5° C., typically at a selected temperature that is kept within a clinical tolerance range, e.g., ±10% or ±5%. The inlet and outlet conduit orifices can be disposed relative to each other such that the entire region of interest is maintained at the desired temperature. In certain embodiments, the cold air will be administered from between approximately 1 minute to approximately 75 minutes; the specific amount of time depends on the patient's anatomy (i.e., the target amount of adipose tissue reduction) and clinical factors determined to bear on the likely responsiveness of the patient's tissue to treatment.

Figure 8A:
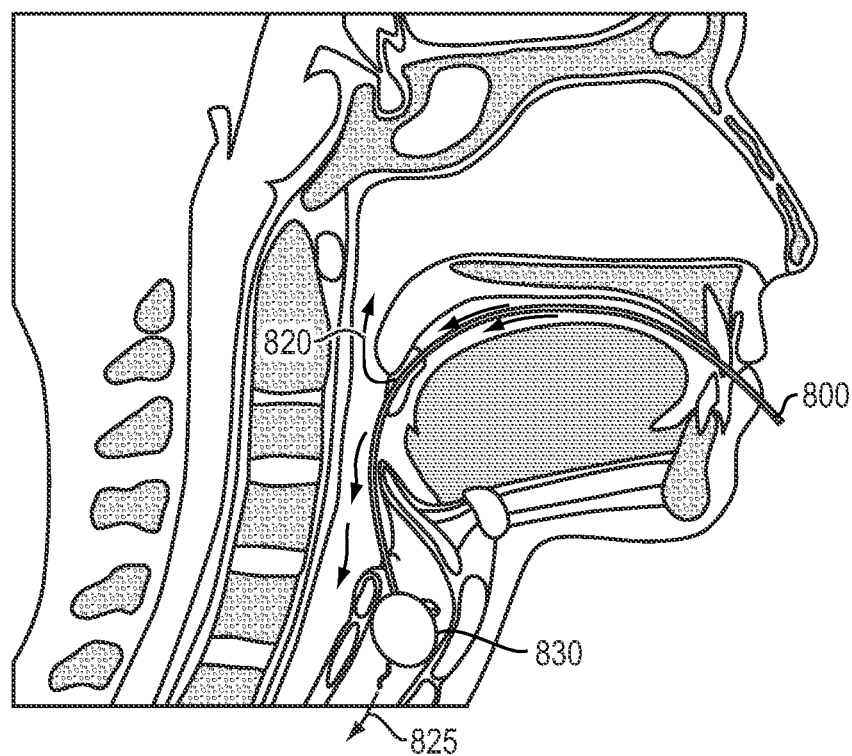
FIG. 8A depicts a side cross-sectional view of a human patient and a eighth exemplary embodiment of a cooling device.
Figure 8B:
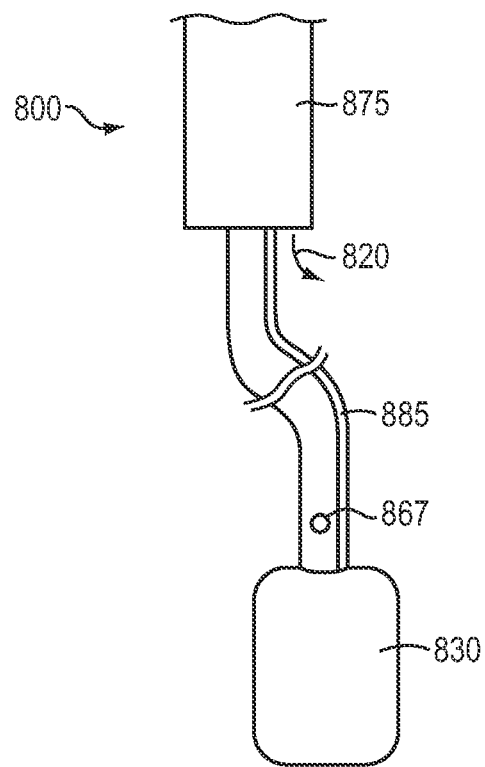
FIG. 8B schematically depicts the tubing arrangement of the eighth exemplary embodiment shown in FIG. 8A.
Figure 8C:
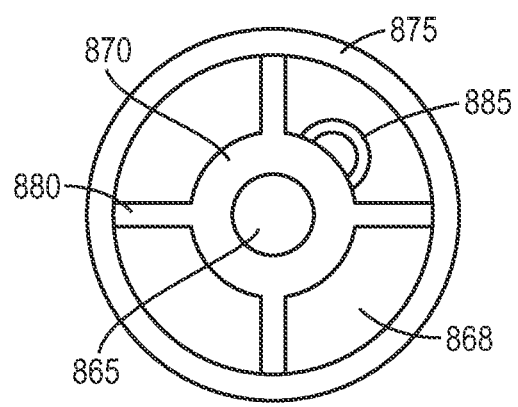
FIG. 8C depicts an end view of the tubing arrangement of the eighth exemplary embodiment shown in FIG. 8A.

Alternatively, as depicted in FIGS. 8A-8C, rather than utilizing separate air delivery and withdrawal tubes, a dual-lumen tubular member 800 that provides both cold air 820 to the oropharynx and breathing air 825 to the lower respiratory tract may be employed. An inflatable member 830 can be used to seal the esophagus so that cold air 820 is restricted from entering the lower respiratory tract. In certain embodiments, dual-lumen tubular member 800 comprises an outer lumen 860 that allows cold air 820 to enter the oropharynx, and an inner lumen 865 that allows breathing air 825 to be delivered to the lower respiratory tract via a port 867. The tube 870 surrounding the inner lumen 865 includes the inflatable member 830 and is longer than the tube 875 surrounding the outer lumen 860, from which cold air 820 exits. As shown in FIG. 8C, these coaxial tubes 870, 875 may be kept separate (to establish and maintain the outer lumen 860) by means of ribs 880 running between the tubes. An inflation tube 885 running along the inner 870 (but fluidly independent thereof) facilitates inflation of the inflation member 830 by the clinician, e.g., via a bulb or by a pump within cooling unit 40. This configuration may be used in the embodiments shown in FIGS. 7 and 9 as well.

Figure 9:
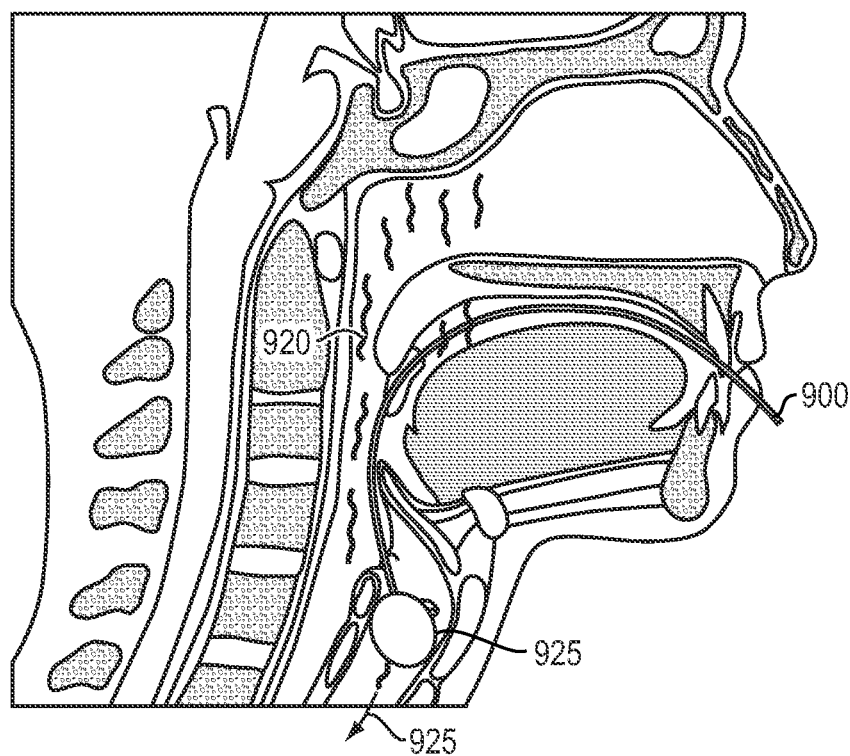
FIG. 9 depicts a side cross-sectional view of a human patient and a ninth exemplary embodiment of a cooling device.

With reference now to FIG. 9, a cold liquid 920 can be administered to an intubated patient in a manner similar to cold air in the embodiments shown in FIGS. 7 and 8. In exemplary embodiments the liquid is biocompatible with a freezing point less than water, e.g., an aqueous glycerin solution. The oral cavity/oropharynx is filled with the cold liquid 920, and an inflatable member 925 is inflated on the intubation tube 900 to prevent aspiration. The liquid may be continuously replenished or left in place. In certain embodiments, the temperature of liquid 920 is approximately −20 to approximately 0° C., or more generally, maintained between approximately −25° C. and 5° C., typically at a selected temperature that is kept within a clinical tolerance range, e.g., ±10% or ±5%. between approximately −20 and approximately 0° C. and left in place or continually circulated for approximately 1 minute to approximately 75 minutes; the specific amount of time depends on the patient's anatomy (i.e., the target amount of adipose tissue reduction) and clinical factors determined to bear on the likely responsiveness of the patient's tissue to treatment.

The various illustrative embodiments of devices, systems, and methods described herein are not intended to be limited to the particular forms disclosed. Rather, they include all modifications and alternatives falling within the scope of the claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A device for treatment of obstructive sleep apnea, the device comprising:
   a. a cooling unit for chilling a cooling fluid; and
   b. an applicator for receiving the cooling fluid, the applicator comprising an engagement member configured for contact with oropharyngeal tissue, wherein the engagement member is shaped to be complementary to a target portion of the oropharyngeal tissue, the applicator comprising a recirculation conduit for facilitating heat transfer between the engagement member and the cooling fluid,
   the applicator and cooling unit being configured to cooperatively cause cooling of the oropharyngeal tissue by placement of the engagement member in contact with a surface of the oropharyngeal tissue, the engagement member being configured to be cooled to a temperature between approximately 5° C. and approximately −25° C. during contact for a time sufficient to cause cryolysis of adipose tissue within the oropharyngeal tissue, and thereby reduce a volume of said adipose tissue.

2. The device of claim 1, wherein the engagement member comprises a flexible and conformal material.

3. The device of claim 1, wherein the engagement member comprises a hinge, the applicator further comprising a control member configured to facilitate closure of the engagement member, via the hinge, to grasp tissue.

4. The device of claim 1, wherein the engagement member comprises a substantially flat plate.

5. The device of claim 1, wherein the engagement member comprises a "C"-shaped member configured to be complementary to a base of a tongue.

6. The device of claim 1, wherein the engagement member is comprises a "V"-shaped member configured to engage a soft palate or a uvula.

7. The device of claim 1, wherein the cooling unit is configured to provide suction to the engagement member to enhance mechanical contact thereof with the oropharyngeal tissue.

8. The device of claim 1, wherein the cooling fluid comprises a liquid.

9. The device of claim 8, wherein the liquid comprises a refrigerant.

10. The device of claim 8, wherein the liquid comprises a water and glycerine solution.

11. The device of claim 1 wherein the cooling unit is configured for feedback operation to maintain a substantially constant temperature at the target portion of the oropharyngeal tissue.

12. The device of claim 11, wherein the applicator further comprises a temperature sensor, the cooling unit being configured to be responsive to the sensor.

13. A device for treatment of obstructive sleep apnea, the device comprising:
   a. a cooling unit for chilling a cooling fluid; and
   b. an applicator for receiving the cooling fluid from the cooling unit, wherein the applicator comprises a needle configured for injection of the cooling fluid into oropharyngeal tissue.

14. The device of claim 1 wherein the cooling fluid comprises chilled air.

15. A device for treatment of obstructive sleep apnea, the device comprising:
   a. a cooling unit for chilling air; and
   b. an applicator for receiving chilled air from the cooling unit, wherein the applicator comprises a tube configured for introducing the chilled air into the oropharynx; and an inflatable member configured for sealing the esophagus and preventing the chilled air from entering the lower respiratory tract.

16. The device of claim 15 wherein the tube comprises inner and outer coaxial lumens, the inner lumen having a portion extending past an end of the outer lumen and having an inflatable member thereon, the cooling unit being configured for sending chilled air through the outer lumen and breathable air through the inner lumen.

17. A device for treatment of obstructive sleep apnea, the device comprising:
   a. a cooling unit for chilling a biocompatible liquid; and
   b. an applicator for receiving chilled biocompatible fluid from the cooling unit, wherein the applicator comprises a tube configured for introducing the chilled biocompatible liquid into the oropharynx and an inflatable member configured for sealing the esophagus and preventing aspiration of the chilled biocompatible liquid.

18. The device of claim 1, wherein the engagement member is configured to be placed in contact with the surface of the oropharyngeal tissue between approximately one minute and approximately thirty minutes to cause cryolysis of adipose tissue within the oropharyngeal tissue, thereby reducing the volume of said adipose tissue.

* * * * *